(12) United States Patent
Shanbhag

(10) Patent No.: US 11,250,935 B2
(45) Date of Patent: Feb. 15, 2022

(54) DRUG DOSAGE ASSISTANT

(71) Applicant: CERNER INNOVATION, INC., Kansas City, KS (US)

(72) Inventor: Anand Parmeshwar Shanbhag, Bangalore (IN)

(73) Assignee: Cerner Innovation, Inc., Kansas City, KS (US)

( * ) Notice: Subject to any disclaimer, the term of this patent is extended or adjusted under 35 U.S.C. 154(b) by 922 days.

(21) Appl. No.: 15/393,480

(22) Filed: Dec. 29, 2016

(65) Prior Publication Data

US 2018/0189458 A1  Jul. 5, 2018

(51) Int. Cl.
*G16H 10/60* (2018.01)
*G16H 20/10* (2018.01)
*G16H 40/67* (2018.01)

(52) U.S. Cl.
CPC ............ *G16H 10/60* (2018.01); *G16H 20/10* (2018.01); *G16H 40/67* (2018.01)

(58) Field of Classification Search
CPC combination set(s) only.
See application file for complete search history.

(56) References Cited

U.S. PATENT DOCUMENTS

| | | | |
|---|---|---|---|
| 5,486,222 A * | 1/1996 | Hauner | |
| 6,305,377 B1 * | 10/2001 | Portwood et al. | |
| 6,317,719 B1 | 11/2001 | Schrier et al. | |
| 7,805,385 B2 | 9/2010 | Steck et al. | |
| 7,844,560 B2 | 11/2010 | Krishnan et al. | |
| 8,579,784 B2 | 11/2013 | Krishnan et al. | |
| 8,688,468 B1 | 4/2014 | Dacosta et al. | |
| 8,781,855 B2 | 7/2014 | Miller et al. | |
| 2002/0040282 A1 * | 4/2002 | Bailey et al. | |
| 2004/0010425 A1 * | 1/2004 | Wilkes et al. | |
| 2005/0055242 A1 * | 3/2005 | Bello et al. | |
| 2006/0047538 A1 * | 3/2006 | Condurso et al. | |
| 2009/0281835 A1 * | 11/2009 | Patwardhan et al. | |
| 2010/0324936 A1 * | 12/2010 | Vishnubhatla et al. | |
| 2016/0030683 A1 * | 2/2016 | Taylor et al. | |
| 2016/0300037 A1 * | 10/2016 | Mould | |
| 2017/0255758 A1 * | 9/2017 | Washko | |

* cited by examiner

*Primary Examiner* — Michael Tomaszewski
*Assistant Examiner* — William T. Monticello
(74) *Attorney, Agent, or Firm* — Shook, Hardy & Bacon L.L.P.

(57) ABSTRACT

Methods, systems, and computer-readable media are provided for computer based healthcare information are provided that automatically calculate a recommended drug dosage for an individual. The system has a computer data store including drug dosage information and individual data. The dosage information includes a target dose, dosage algorithms and rounding rules for the drug. The individual data from the individual's medical records includes individual identification, weight, height and lab results. The system includes a computer processor coupled to the computer store programed to receive the drug dosage information and the individual data and process the dosage algorithm and target dose with the individual's height and weight to calculate a recommended drug dosage for the individual.

17 Claims, 17 Drawing Sheets

FIG. 5.

Date of birth
    Date of birth: 06/06/1984 (31 Years)
        a. DOB
            i. Value shall be pulled from the patient information.
            ii. Value shall be presented as MM/DD/YYYY format.
            iii. Calculated age in years should be shown.
            iv. Value should not be editable.

Sex
    Sex: Male
        a. Gender
            v. Value shall be pulled from the patient information.
            vi. Value should not be editable.

Race
    Race: White
        a. Race
            vii. Value shall be pulled from the patient information.
            viii. Value should not be editable.

Height
    Height: [  cm  ]
        a. Value
            ix. Value shall be pulled from the patient information.
            x. Value shall be presented whole numbers.
            xi. Value shall be editable.
        b. Unit
            xii. Value shall be pulled from the patient information.
            xiii. Value shall be presented as centimeters (cm).
            xiv. Value should not be editable.

*FIG. 6.*

Source

Source: [None]

i. Value shall be pulled from the patient information.
    ii. Value shall be presented with the date time stamp.
    iii. If value is not available (None) is displayed.
    iv. Value should not be editable.

Actual weight

Actual weight: 81.818 kg a. Value
    i. Value shall be pulled from the patient information.
    ii. Value shall be presented whole numbers.
    iii. Value shall be editable.
  b. Unit
    iv. Value shall be pulled from the patient information.
    v. Value shall be presented as Kilograms (Kg).
    vi. Value should not be editable.

Source

Source: 1/13/2016 9:58 AM  81.818 kg Weight Dosing i. Value shall be pulled from the patient information.
    ii. Value shall be presented with the date time stamp.
    iii. If value is not available (None) is displayed.
    iv. Value should not be editable.

Adjusted weight

Adjusted weight: 81.818 kg a. Value
    vii. Value shall be pulled from the patient information.
    viii. Value shall be presented whole numbers.
    ix. Value shall be editable.
  b. Unit
    x. Value shall be pulled from the patient information.
    xi. Value shall be presented as Kilograms (Kg).
    xii. Value should not be editable.

6a. Adjustment

Adjustment: Actual (no adjustment) 

i. Value shall default to Actual (no adjustment) when the value is equal to actual weight.

*FIG. 7.*

Dose values

Dose Values

1) Target dose: 1 mg/kg

2) Calculated dose: 81.818 mg

3) Dose Adjustment: 81.818 mg  100 %  0.9778 mg/kg

4) Final dose: 80 mg

5) Standard dose: mg/kg

6) Rounding rule: mg

7) Adjust Reason: Manually Entered

8) Route: IV Piggyback

*FIG. 9.*

Target dose:
1) Target dose [ 1 ] [ mg/kg ▼ ]
   a. Dose
      i. Value shall be pulled in form the service being ordered.
      ii. Field should be editable.
      iii. Field should allow only numbers and decimals as per the preference set
      iv. Filed should be editable when subsequent actions of renew, revise are carried out
   b. Unit
      i. Value shall be pulled in form the service being ordered.
      ii. Field should be editable via a drop down containing the standard normalized dose units.
      iii. Field should not allow manual entry of values
      iv. Field should be editable when subsequent actions of renew, revise are carried out Calculated dose:
2) Calculated dose [ 81.818 ] [ mg ]
   a. Dose
      i. Value shall be calculated by using the height and weight from their respective fields
      ii. This shall not be editable by the user
   b. Unit Shall use the unit of weight

*FIG. 10.*

Dose Adjustment:

3) Dose Adjustment: 81.818 mg  100 % a. Dose
      i. Value shall be populated from the calculated dose
      ii. This shall not be editable by the user
   b. Unit
      i. Shall be populated from the calculated dose unit
   c. Percentage
      i. Value shall be defaulted to 100% when the Final dose value is equal to calculated dose or empty
      ii. Value shall be calculated to reflect the percentage of variation between the calculated dose and the Final dose if Final value field is valued.

Final dose:

4) Final dose: mg  0.3778 mg/kg a. Dose
      i. Field shall be blank by default
      ii. Field should allow only numbers and decimals as per the preference set
   b. Unit
      i. Value shall be a weight unit
   c. Normalized dose
      i. Value shall be calculated to reflect against the Target dose
   d. Unit
      i. Value shall be a Normalized dose unit as per Target dose Unit.

*FIG. 11.*

Relation between the Final dose and the percentage

3) Dose Adjustment: 81.818　mg　　100 ▲▼ %
4) Final dose: 50　mg　　0.3778　mg/kg

Final dose and the percentage should be able to reciprocate the changes made to each value Standard dose:

5) Standard dose: ▢　mg ...... ▢ mg/kg a. Dose
   i. Field shall be blank by default.
   ii. Field should allow only numbers and decimals as per the preference set.
b. Unit
   i. Value shall be a weight unit.
c. Normalized dose
   i. Value shall be standard normalized dose.
d. Unit
   i. Value shall be a standard normalized dose unit.

*FIG. 12.*

Lab values

This would be a collection of all the test results done for the given patient and would pull in the relevant lab results based on the medication being administered.

Serum creatinine

Serum creatinine: [ 0.9 ]  mg/dL a. Value
   i. Value shall be pulled from nursing.
   ii. If value is not available then it will default to a blank
   iii. Value shall be editable.
b. Unit
   i. Value shall be pulled from nursing.
   ii. Value shall be presented as milligrams/deciliter (mg/dL).
   iii. Value should not be editable.

Source

Source: [ 1/15/2016 8:55 AM 0.90 mg/dL Creatinine Lvl ]

i. Value shall be pulled from the patient information.
   ii. Value shall be presented with the date time stamp.
   iii. If value is not available (None) is displayed.

Value should not be editable.

*FIG. 14.*

CrCl(est)

CrCl (est.): 137.63 mL/min a. Value
   i. Value shall be calculated using the default algorithm in preference.
   ii. If value is not available then it will default to a blank
   iii. Value shall be editable.
b. Unit
   iv. Value shall be presented as milliliters/minute (mL/min).
   v. Value should not be editable.

8a. Algorithm

Algorithm: Cockroft-Gault (Actual Weight) ⌄ a. Value
   i. This shall be a drop down field.
   ii. User shall be able to select the different algorithms set in the preference.

8b. Weight used for calculation

Weight Used for CrCl: Actual weight   81.818 kg a. Value
   i. Value shall be pulled from the patient information.
   ii. The weight used shall be displayed next to this field

*FIG. 15.*

DRUG DOSAGE ASSISTANT

BACKGROUND

Currently, drug dosages are calculated manually by doctors in a healthcare setting or a "one size fits all" or standard dosage is prescribed to all individuals. This is particularly problematic for the pediatric or geriatric age group where the size of the patient may vary and a standard or manually calculated dosage could be incorrect and even dangerous.

This method also is problematic for the prescription of high acuity drugs and drugs with a narrow therapeutic zone or window, for example the drugs used for the treatment of cancer. In addition, typically if a drug at the standard dose is found to be incorrect, the typical method is to stop the administration of the drug.

BRIEF DESCRIPTION OF THE DRAWINGS

FIG. 5 is a graphical user interface depiction for entry of reference data to be utilized by the dosing assistant system;

FIGS. 6-8 are data entry flows for entry of items of reference data to be utilized by the dosing assistant system;

FIG. 9 is a graphical user interface depiction for entry and calculation of dosage values of the dosing assistant system;

FIGS. 10-16 are data entry flows for entry of items to be entered and utilized for calculation of dosage values by the dosing assistant system.

SUMMARY

Figure 1:
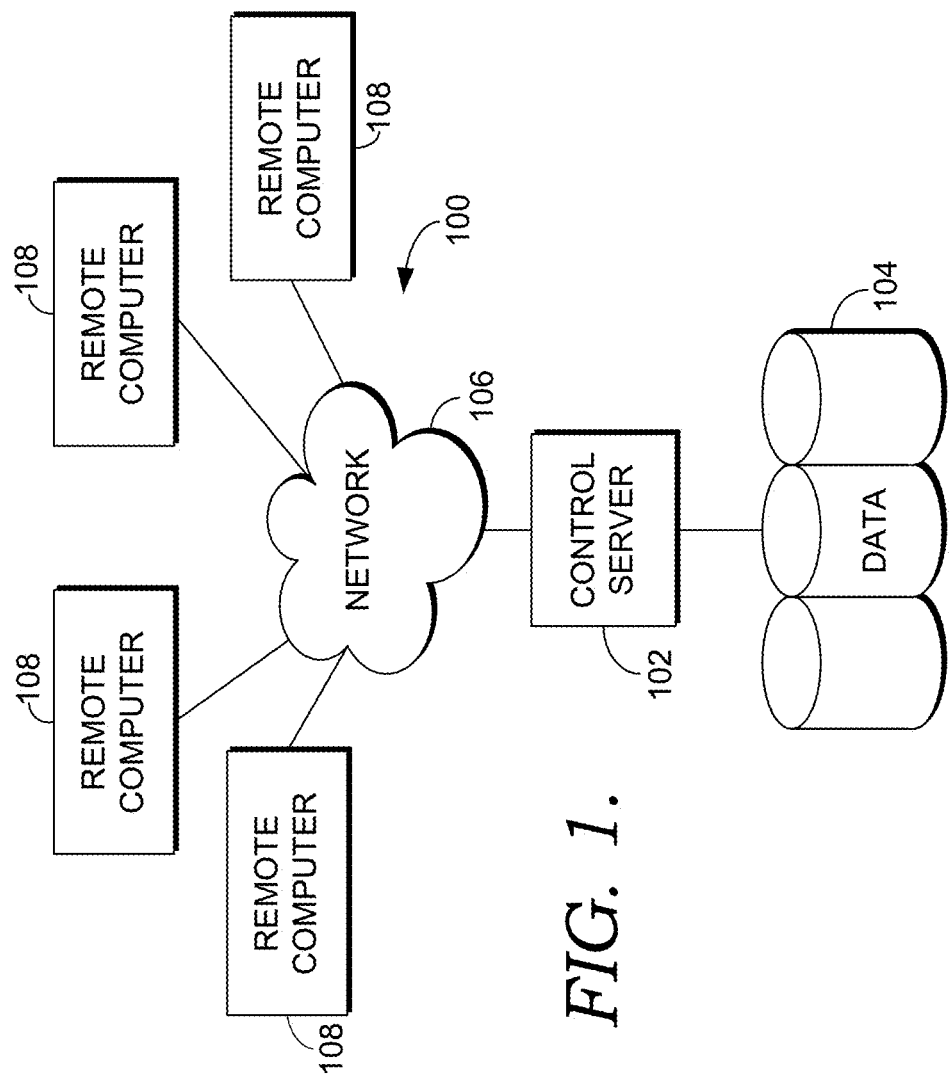
FIG. 1 is a block diagram of an exemplary computing environment suitable to implement embodiments of the present invention.

The dosing assistant system described provides users with recommended dosage calculation for a drug being prescribed to an individual. The system has a computer data store including drug dosage information and individual data. The dosage information includes a target dose, dosage algorithms and rounding rules for the drug. The individual data from the individual's medical records includes individual identification, weight, height and lab results. The system includes a computer processor coupled to the computer store programed to receive the drug dosage information and the individual data and process the dosage algorithm and target dose with the individual's height and weight to calculate a recommended drug dosage for the individual.

A computer system and method for preventing an electronic medical order for drug doses that exceeds an upper threshold for medical individual safety. The drug being dosed to the individual is received from a computer interface with a doctor. The target dose, upper limit dosage and dosage algorithm are received from a computer data store along with the individual's height and weight from patient records. The dosage algorithm and target dose along with the individual's height and weight to calculate a recommended dosage for the individual.

The doctor inputs in a drug dosage for the individual that differs from the recommended dosage. The dosing assistant computer system processes the input drug dosage and the recommended drug dosage to the upper limit for the drug to determine the input drug dosage exceeds the upper limit for the drug and provides and interface with a graphical indicia indicating to the doctor that the input drug dosage exceeds the upper limit for the drug.

The claimed solution is necessarily rooted in computerized electronic medical record technology in order to overcome a problem specifically arising in the realm of computer healthcare information networks, and the claims address the problem of efficiently and correctly providing the drug doses specific to an individual being treated. If adhering to the routine, conventional function of providing a medical dosage in a computerized electronic medical record technology, a standard dose would be provided for all individuals regardless of the individual's weight, surface area and without knowledge of the type, acuity and therapeutic index of the drug. The claimed invention overcomes the limitations of current computer healthcare information technology and provides other benefits that will become clear to those skilled in the art from the foregoing description.

The claimed computerized system and method of the present application represents a new paradigm of providing drug dosage based on precision or individualized medicine. Not only does the claimed invention provide correct drug dosage information but it also prevents errors in entry of the information and saves the user significant time. Users of electronic medical records or electronic health records utilizing the claimed invention will notice increased performance of their EMR or EHR, increased retrieval of the medication information from storage, fewer user steps to utilize the EMR and user access to the medication information. Furthermore, anything that reduces the number of "clicks" or entries a computer or mobile device user has to make in an EMR or EHR or to enter medication reminders results in reducing the memory utilization, CPU cycles, number of operations that need to be performed by the computer, and power consumption. The resulting cost savings and operational efficiencies of a computer electronic medical record magnify the potential benefits of this technology.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention are directed to methods, systems, and computer-readable media for a system and method for automatically calculating and recommending a dosage drug to a doctor for an individual. Embodiments are further directed to reducing medical error by notifying a dosing doctor that the dosage of the drug has exceeded the upper threshold for toxicity for the drug being dosed.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention is a special computing system that can leverage well-known computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of non-transitory computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home medical environments, and clinicians' offices. Clinicians may comprise a treating doctor or doctors; specialists such as surgeons, radiologists, cardiologists, and oncologists; emergency medical technicians; doctors' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire medical community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a microphone (e.g., voice inputs), a touch screen, a pointing device (commonly referred to as a mouse), a trackball, or a touch pad. Other input devices comprise satellite dishes, scanners, or the like. Commands and information might also be sent directly from a remote medical device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
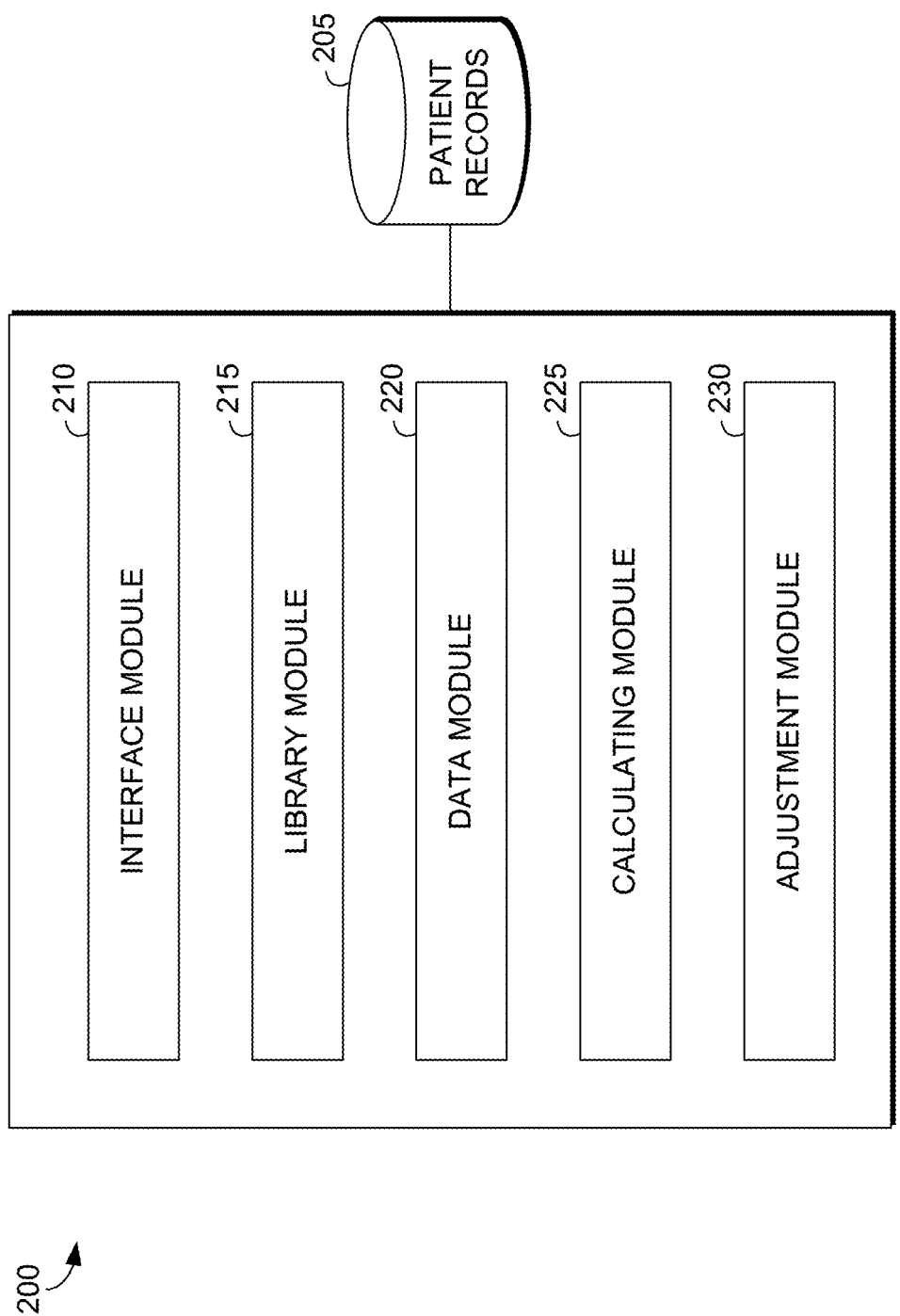
FIG. 2 is an exemplary system architecture suitable to implement embodiments of the present invention.

Referring to FIG. 2, a system and method to provide a doctor with an ability to customize the dosage of a drugs in a computer medical record environment. A drug is a medicine or other particle or substance which has a physiological effect when ingested or otherwise introduced into the body. The dosage assistant 200 is in communication with a doctor order entry system (CPOE) to enter a drug order for an individual in a medical setting. Dosage assistant 200 includes interface module 210, library module 215, data module 220, calculating module 225 and adjustment module 230. The data module 220 of dosage assistant 200 is in communication with patient records 205 which include electronic medical records and electronic health records accessed via a network. Patient records 205 may be maintained in a record database, such as Cerner Millennium database.

Interface Module 210

Figure 3:
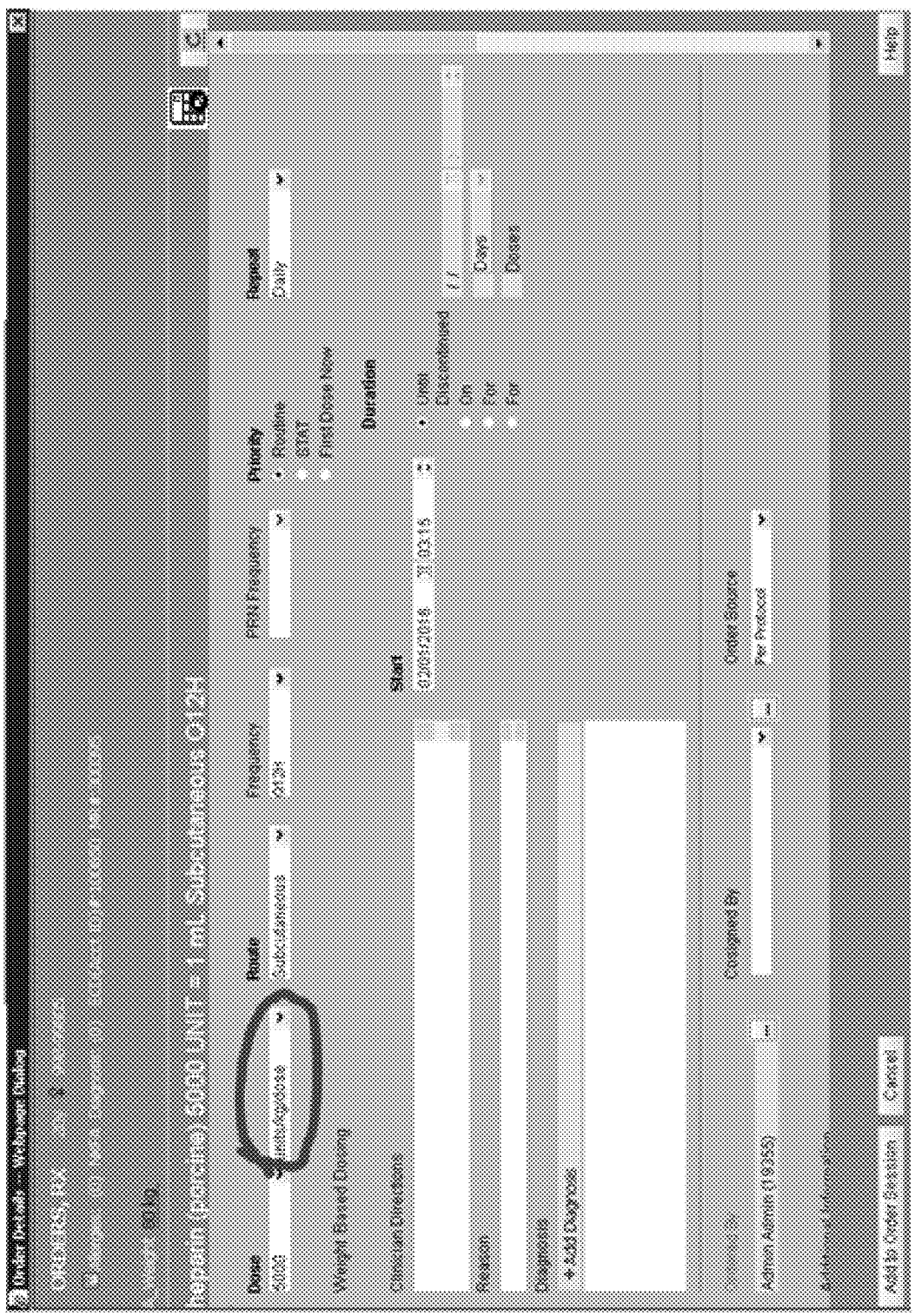
FIG. 3 is a graphical user interface depiction of user order entry flow for launching the dosing assistant system from a medical order entry.

A user, such as a doctor, interacts with graphical user indicia of interface module 210 to view and input information regarding a drug dosage for an individual. For example, from a drug order entry interface as shown in FIG. 3, the doctor can launch the interface module 210 of dosing assistant as shown in FIG. 4 by selecting a dosing assistant icon as shown in the upper right corner of FIG. 3.

The dosing assistant system 200 utilizes interface module 210 to disclose data specific to route of administration, indication, dose type (e.g., prophylactic, maintenance and single dose), and special conditions (e.g., hepatic insufficiency, concomitant thiazide diuretic therapy, and radiation therapy).

Figure 4:
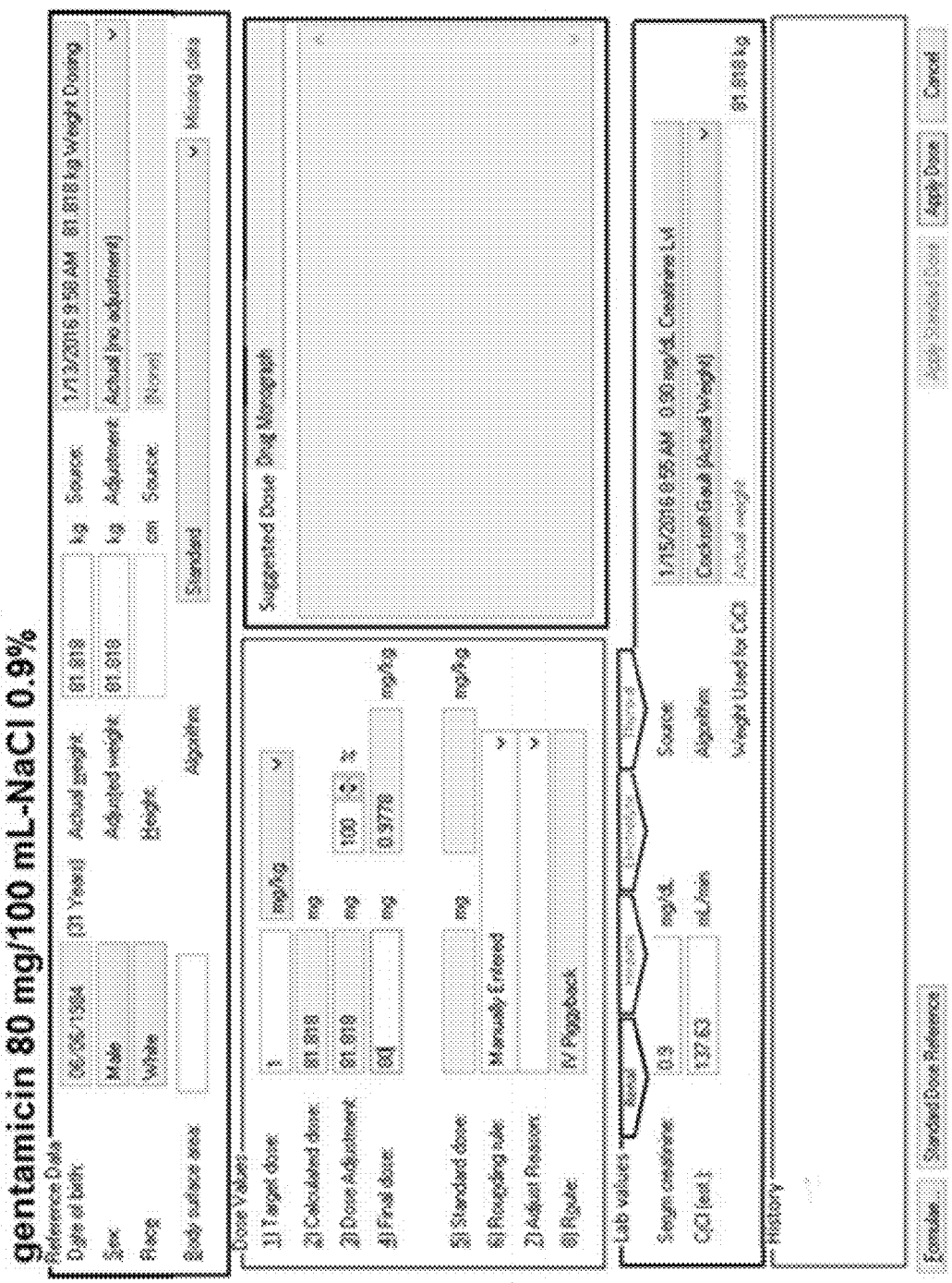
FIG. 4 a graphical user interface depiction for entry of information to be utilized by the dosing assistant system.

A variety of information can be displayed and input into the interface module 210 as shown in FIG. 4. Information regarding the drug displayed can include the drug monograph, suggested dosage for the drug, route and order history of the drug. The monograph for the selected drug which includes detailed information about the drug including the kinds and amounts of ingredients it may contain, the conditions and limitations for which it may be offered, storage, directions for use, warnings, interactions, warnings and other label information. The drug monograph may contain important information concerning interactions with other drugs and a calculated body surface area.

Figure 5:
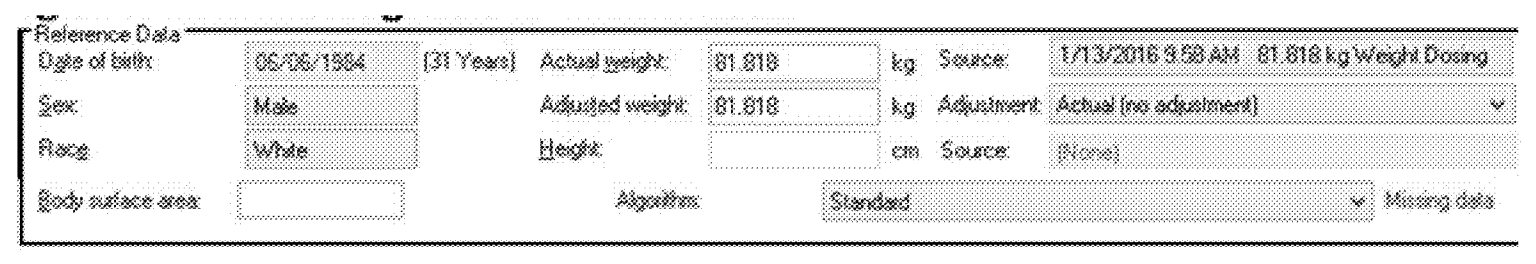

Interface module 210 may display reference data for the patient as shown in FIG. 5, such as date of birth, sex, race, actual weight, height, adjusted weight. Addition information that can be displayed via interface module 210 includes patient lab values, including serum creatinine and CrCL estimates.

The graphical indicia of interface module 210 is user interactive. The doctor can choose algorithms applied for calculating dosages for an individual based on body weight and body surface area. A doctor may leverage the graphical indicia of interface module to override a standard or calculated dose for the individual and provide textual reasons for overriding the calculated or suggested dosage.

Providing individual's medical data and the drug monograph via interface module 210 enhances doctors' ability to screen drug doses by considering individual-specific, clinically relevant parameters. This is important to a doctor for dosing high acuity drugs with narrow therapeutic ranges. Thus, the dosing assistant 200 accommodates inter-patient variability and prevent generalized dosing of medication. The dosing assistant can compare the calculated final dose can be leveraged to determine inappropriate dosing and duration of therapy and an alert can be triggered via interface module 210 to notify the doctor of such.

Data Module 215

Data module 215 typically obtains values for an individual from patient records 205 or they may be entered by doctor when using calculator. Data module 215 gathers data for the individual including date of birth, sex, race, height (in units), weight (in units) of individual which are typically not editable once obtained from patient records 215 in FIGS. 6-7. Data module 215 also identifies the source of the values along with a date time stamp. The data module 205 also may provide a field with weight called actual weight that is editable by a doctor.

Data module 205 also obtains lab values for an individual as shown in FIGS. 14 and 15. These would include a collection of test results for a given individual. These would be flexible depending on the drug being administered to the individual. The lab values may include serum creatinine and Cr Clest and may be editable by the doctor as shown in FIG. 4. This includes data regarding creatinine clearance of the individual by the interface module 210 within the dosing assistant 200. The preference for which calculation to use for an estimate of renal function and altered by the user as appropriate via interface module 210.

Other lab results for the individual include estimated glomerular filtration rate (eGFR) within the interface module of dosing assistant. The preference for which calculation to use for an estimate of renal function and altered by the user as appropriate. Decision support rules obtained from the library module 215 can continue to monitor and alert the user to amend dosages/administration intervals as and when blood levels are resulted.

Figure 16:
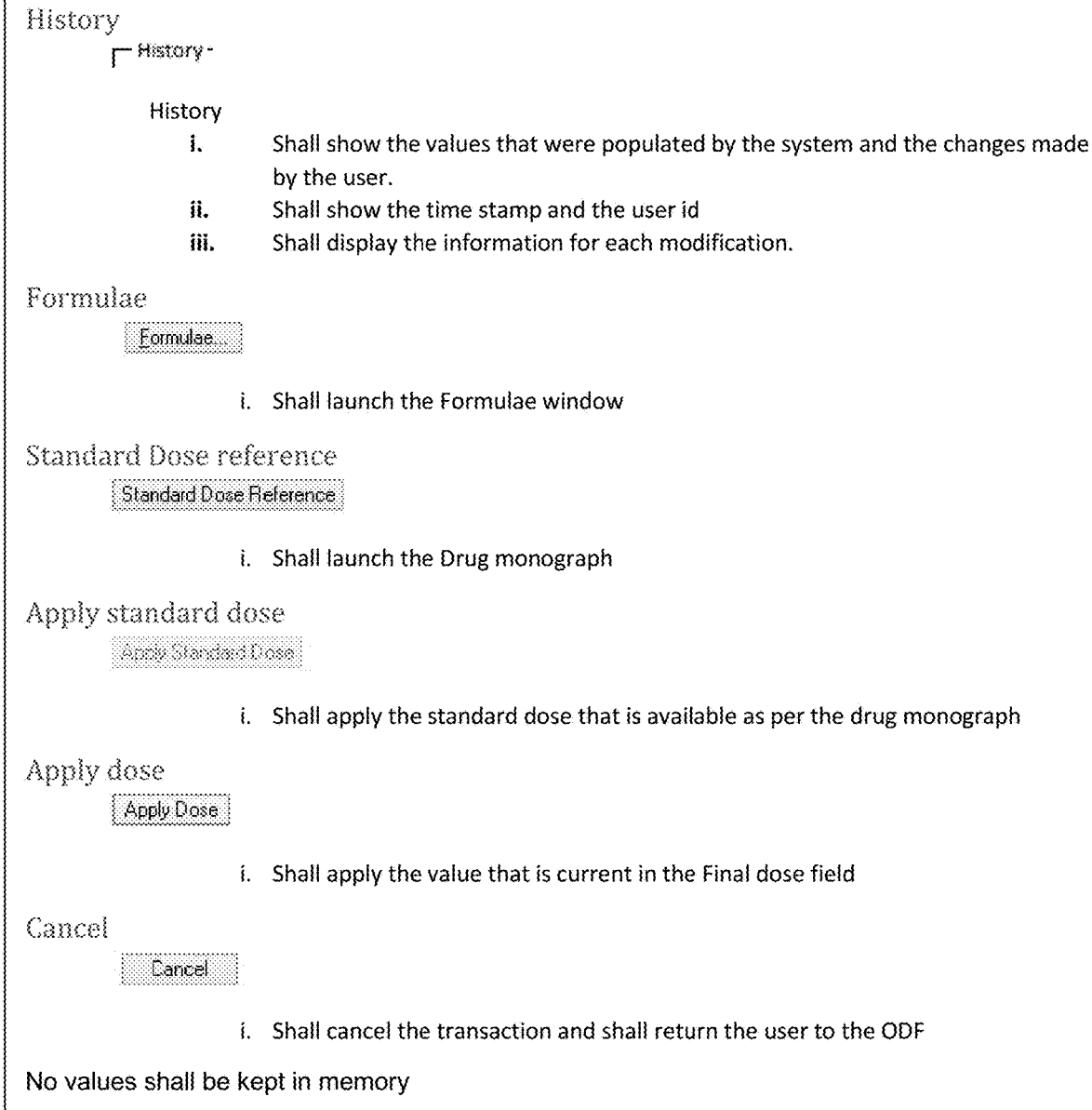

The interface module 210 provides a text box as shown in FIGS. 4 and 9 for doctors to provide comments regarding reasons for adjustment of a drug dosage and relevant information and stores these comments in data module 220 and patient records 205 as a part of the medication history as shown in FIG. 16 if needed in the future for auditing or reference.

Data module 205 also tracks and stores changes made to values via the interface module 210 for the individuals including who made changes and a date time stamp for changes to the values. For example, each entry of a patient's height and weight is date, time and user stamped and is visible in the interface module 210 of dosing assistant 200.

Library Module 215

Figure 8:
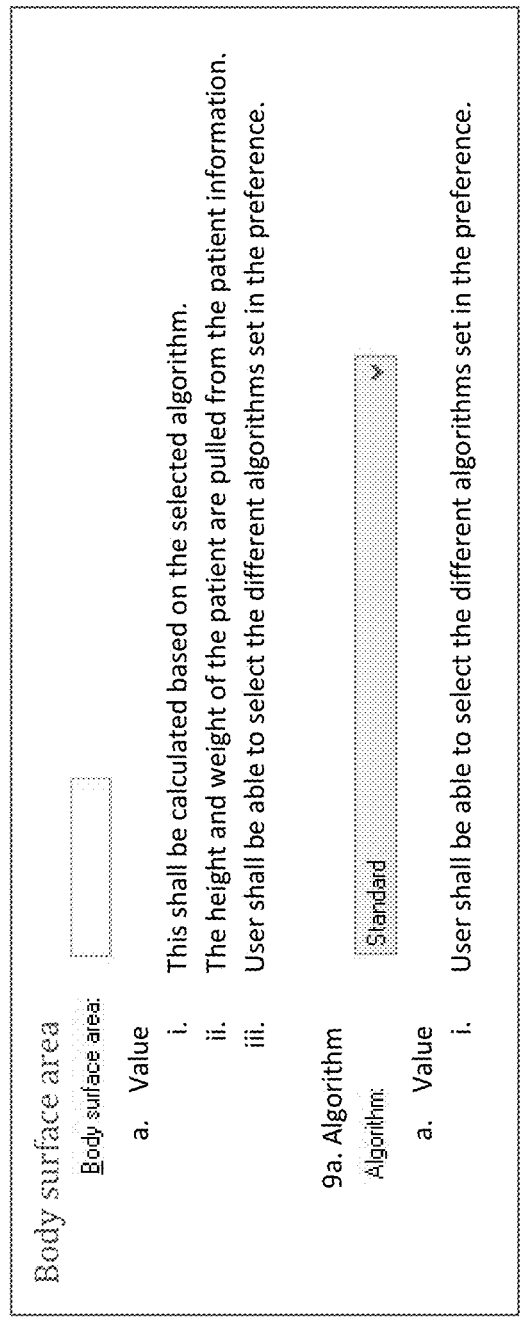

Library module 215 contains a computer database library of information relating to the drug being dosed, applicable algorithms for determining body weight and body surface area for the drug being dosed, target dose, dosage upper limits, rounding and adjustment rules and decision support rules for monitoring lab results and alerting a doctor via interface module 210 when results are out of range. The information includes dosing algorithms by weight and body surface area as shown in FIGS. 8-10. Library module 215 stores the appropriate algorithms that may be applied by calculating module 225 to drug or particular patient characteristics based off of patient values from data module 205. In addition, library module 215 includes the target dose for a drug shown in FIG. 10. For example, with reference to FIG. 4, the target dose of gentamicin is 1 mg/kg based on an individual's weight. For example, a body surface area algorithm may apply to a high acuity drug while a weight calculation may apply based on age of the patient obtained from data module 205. Furthermore, the weight algorithm uses the actual weight value from the data module. A doctor is able to select the desired algorithm from interface module 210 based on preference.

The library module 215 includes drug order specific upper dose limit for dose calculations to facilitate clinician workflow within dose calculator including active strength and volume units. The upper limit on the drug orders in the dosing assistant 200 ensures a safe dose and compliance with accepted practice standards. If the final dose is less than the defined upper limit, no indication of the upper limit is displayed by the interface module 210. If the final dose exceeds the upper limit defined, the final dose is set to the upper limit and the doctor is notified that of the upper limit. The history of the upper limit is stored in data module 220 and communicated to patient records 205. If the upper limit is applied by the calculating module 225, a no rounding rule is applied as discussed in more detail below. The library module 215 also includes decimal precision is set up beyond what is allowed by the dose calculator, the value will be rounded as appropriate (2 for volume, 4 for strength).

In one embodiment, a doctor can override the upper limit via interface module 210 to customize to the specific patient scenario using clinical judgment. If a user overrides the upper dose limit, the rounding rule gets set to manually entered. The data module 220 stores the last dose calculation data to reflect the fact that maximum dose specified by the library module has been overridden when the final dose was calculated. Dose calculation history of data module 220 as shown in FIG. 16 should reflect the fact that user chose to override the maximum dose set by the system. Thus, how often a particular provider overrides the maximum dose can be monitored for clinician compliance with best practices defined in the system.

Calculating Module 225

The dose assistant system 200 of a drug order entry computer system is a valuable tool for utilizing the calculating module 225 for calculating medication dosages based on patient lab values and measurements. Calculating module 225 is useful for prescribing and administration of drugs where the therapeutic index (the therapeutic zone or window) is very narrow, this is particularly true of drugs used to treat cancer and in the light of the regulatory roadmap for precision medicine. The calculating module calculates drug dosages for the pediatric and the geriatric age group where the patient may be underweight/overweight with regards to the percentile and dose correction would be needed.

Calculating module 225 calculates the dosage of a drug to be administered and customize it based on the patient's weight, body surface area or the relevant lab values (such as serum creatinine). The system and method allows for customization based on the individual's weight, height and body surface area. The method and system will give the doctor an ability to view the relevant laboratory result values from patient records 205 via interface module 210 for an individual to help the doctor to tailor the dose rather than the usual method of stopping the medication.

Calculating module 225 incorporates individual values from data module 210 when determining normalized dose calculation. Access to the calculating module resides within the ordering conversation of interface module 210 so that the doctor can process dose calculations during the ordering process. A preference can be set so that the dose calculator automatically invokes when a normalized dose is entered. For example, the clinician can enter the dose as 5 mg per kilogram and the calculating module 225 automatically will calculate and the interface module 210 displays a 100 mg dose if the patient's weight is 20 kilograms.

Where a drug is required to be dosed by weight a dosing calculator can be launched automatically or by the user. The interface module 210 will display the patient's most recent weight and height, which is date and time stamped. The calculating module 225 calculates the dose based on the target dose from Library module 215 and the adjusted weight which may be the individual's actual, ideal or lean body weight as selected by the prescriber.

Figure 17:
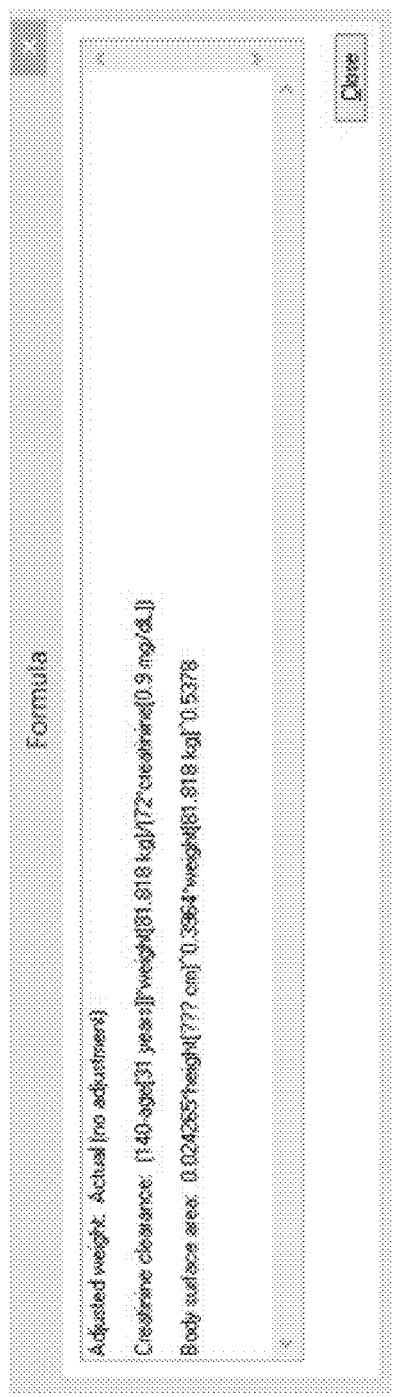
FIG. 17 is a graphical user interface depiction for calculation of dosage values by the dosing assistant system.

The calculating module 225 of dosing assistant 200 calculates body surface area using the multiple formulae as shown in FIG. 17 (hosteller, Dubois & Dubois, Boyd Bradey, Haycock, Gehan and George) accessed from library module 215. The calculator will use the most recent height and weight to calculate the BSA as shown in FIG. 8.

Facilities and user are able to select the different algorithms set in the preference in library module 215. The body surface area or weight algorithm formula applied can be stored in the library module 215 and can be specific to the drug being prescribed or lab results as shown in FIG. 15. Other formulas may be added to the library module 215 to allow new formulas to be added as knowledge for precision medicine and dosing is discovered.

Adjustment Module 230

While the calculating module 225 calculates an appropriate dosing for a drug to an individual taking into consideration individual values and appropriate dosage calculation algorithms, the doctor may still wish to adjust the dosage amount of the drug for the individual Some standard reasons to using the adjustment module 230 to adjust a drug dosage include the medication dose is too high or low, reducing the dose due to serum creatinine level, perioperative loading, postoperative loading, weight adjustment and other medical reasons.

Figure 13:
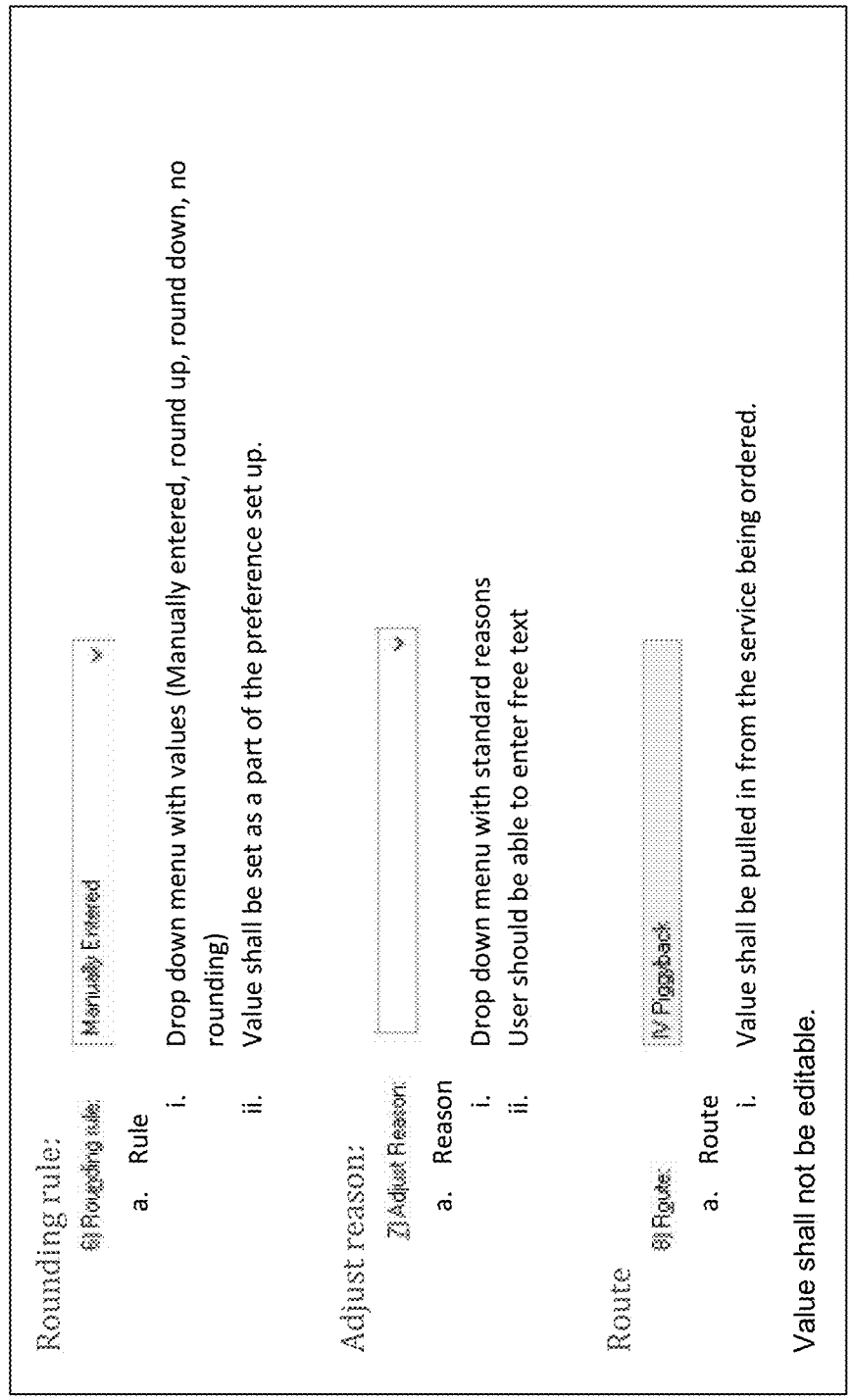

The adjustment module 230 is configured to allow adjustment to drug dosages based on applicable user security levels designated or specialty areas. The doctor can adjust the drug dosage and communicate the reasoning to other members of the individual's medical care team by requesting an adjust reason either by coding or free text entry. For example, if a doctor changes the percent reduction of the dosage may require entry of an adjust reason from the doctor as shown in FIG. 13. When an adjust reason is required to the drug dosage changes, the doctor cannot enter cannot apply or order changes until a reason is provided by coding or free text. When the reason is entered, the changes are tracked and documented and the change in the drug dosage can be entered.

If there is no adjustment between the recommended dosage by the calculating module, no difference is displayed between the calculated dose and final dose and the value of percentage will be 100%. The dose adjustment field in FIG. 4 is automatically populated by the calculated dose along with showing it is 100% of the dosage.

If changes are made by the doctor to the final dose (see FIG. 9) the relation between the final dose and the percentage of the dose adjustment as shown in FIG. 11.

Additionally, a doctor may wish to revise a drug order. Using the adjustment module 230 if an order exists with a normalized dose, when the user selects a revise action the order detail form is displayed with the normalized dose still attached. In order to change the order, the user must refresh the order detail form or use the calculating module of dosing assistant.

The dosing calculator icon is displayed if a normalized dose is selected for the order. If the user cancels out of the calculator, the order detail form is displayed and the normalized dose is still attached to the order.

When an IV Set is ordered, the dose calculator icon is to be displayed for each ingredient in the set when a normalized dose is selected. If the user cancels the calculator, the normalized dose is still attached to that ingredient.

When an order set is ordered, the dose calculator icon is displayed for each item when a normalized dose is selected. The order detail form is displayed and upon selection of a normalized dose the dose calculator is displayed. If the user cancels the dose calculator icon, the normalized dose is still attached to that order. In one embodiment, an order cannot be submitted with a normalized dose attached if the dosing assistant preference is turned on.

The adjustment module 230 of the dosing assistant enables the ordering user to apply rounding functions to achieve a measurable dose. The rounding functions include the abilities to round up, round down, or round to one, two, or three decimal places. Rounding rules can be defaulted to products to ensure an appropriate dosage is always prescribed. The calculating module 225 calculates the appropriate dose based on the individual's weight and the adjustment module 230 rounds to an appropriate dose or use a standard dose as defined in library module 215 or selected by user from interface module 210 if standard premade dosages are used within the hospital.

When setting up rounding rule defaults per drug orderable, the doctor has access to the full list of currently defined available rounding rules. The adjustment module 230 accesses the library module 215 for the default appropriate rounding rule when loading the dose calculator screen for an existing order with specific rounding rule defined. When no default rounding rule defined, default rounding rule as 'No Rounding'. In one embodiment, the user is able to override the default suggested by the system.

In one embodiment, if the drug order is for an IV set, order set, or non-pharmacy order catalog item is selected, the user is unable to define a round rule for the drug order. When a specific rounding rule is set up as inactive it will not be displayed in the dose assistant interface module 210 pick list. When marking an item as inactive, the dosing assistant system will treat an order linked to that item as not having a rounding rule defined (rounding rule field is empty in the dose calculator). In one embodiment, when running dose calculation for an order linked to an inactive rounding rule code value, the dosing assistant does not save a rounding rule to dose calculation history in data module 220.

The doctor can tailor utilizing the interface module 210 of dosing assistant 200 to correctly change the percentage of dosage to be administered to the individual. The calculating module 220 of the dosing assistant 200 calculates the dose to be given based on the percentage that the doctor using the dosing assistant 200. The system and method of the present claimed invention allows the doctor to enter a modified dose and will show the percentage of the actual dose. As described in more detail below, the dosing assistant system also allows a doctor to round of a dose when the calculated dose is not a standard dose as would be in the case of weight based orders. In addition, the interface module 210 displays to the doctor the percentage of deviation from the standard dose as shown in FIG. 12.

With reference to FIG. 3, when a doctor selects a drug, the system will display a dosing assistant icon (RX calculator) to launch the dosing assistant system. Once the dose changes are applied, the dosing assistant icon appears disabled or grayed out and the dose appears in the medication order display line as shown below.

The dose reduction value from past dose calculations in current ordering conversations is stored by data module 220 of dosing assistant. The data module 220 can store the preferences at facility/location or user level to enable defaulting the dose reduction from the last dose calculation into the dose calculator for modify, copy, cancel/reorder, and rewrite actions. When preference is enabled, the dose reduction value from the last dose calculation defaults into dose calculator during modify, copy, cancel/reorder, and rewrite. When previous dose calculation does not exist, default dose reduction as 100% as shown in FIG. 4.

Referring again to interface module 210, a user can override the default dose reduction value. As shown in FIGS. 9-11 the final dose is calculated using the current dose reduction value Current dose reduction value captured and stored in data module 220 and displayed interface module 210 in dose assistant history and last dose calculation. Any changes to the dose reduction percentage are displayed on the history for each medication order that had dose reduction applied in the dose calculator for multiple users to view.

Dose reduction value displayed on the order should be applicable to the most current instance of the doses on the ingredients (note—original order placed with dose reduced to 80%, subsequent modify action removes reduction, no reduction value should be displayed). Multi-ingredient IV sets display dose reduction information per ingredient.

The claimed invention overcomes the limitations of current computer medical information technology and provides other benefits that will become clear to those skilled in the art from the foregoing description.

The invention claimed is:

1. A system useful in a computerized medical system, the system comprising:
   (a) one or more computer stores containing data, for each of a plurality of drugs, defining dosage information corresponding to a drug and data for individuals,
   (i) dosage information corresponding to a drug including target dose, dosage algorithms and rounding rules;
   (ii) data for an individual including individual identification, weight and height;
   (iii) an interface;
   (b) a computer processor on a computing device coupled to the computer store and programmed to:
   (i) receive from the one or more computer data store identification of an individual and the individual's height and weight;
   (ii) receive identification of a drug to be dosed for the individual;
   (iii) receive from the one or more computer data store the target dose, dosage algorithms, and rounding rules for the drug;
   (iv) processing the target dose and dosage algorithm with the individual's height and weight to calculate a recommended drug dosage for the individual;
   (v) processing the rounding rules to calculate an upper limit of the recommended drug dosage for the individual;

(vi) providing for display a dose reduction percentage from a previous dose calculation;

(vii) receiving an input drug dosage via the interface;

(viii) comparing the input drug dosage and the calculated recommended drug dosage to the upper limit of the recommended drug dosage to determine the input drug dosage exceeds the upper limit of the recommended drug dosage; and (ix) based on determining the input drug dosage exceeds the upper limit of the recommended drug dosage, communicating the recommended drug dosage to a clinician via a graphical indicia on the interface indicating the input drug dosage exceeds the upper limit of the recommended drug dosage.

2. The system of claim 1, wherein the dosage algorithm is a weight based algorithm.

3. The system of claim 1, wherein the dosage algorithm is a body surface area algorithm.

4. The system of claim 2, wherein the target dose is a measurement per weight.

5. The system of claim 1, wherein the rounding rule is based on data regarding what is available in an entity's pharmacy.

6. The system of claim 1, further comprising, automatically placing an electronic medical order for the recommended dose for the individual in an electronic medical system.

7. The system of claim 1, further comprising, receiving via an interface an adjustment to the recommended dosage and data regarding reason for the adjustment.

8. The system of claim 7, further comprising storing the adjustment to the recommend dosage in a history log for the individual for the drug.

9. The system of claim 8, further comprising placing an electronic medical order for the adjusted dose for the individual in an electronic medical system.

10. One or more computer storage media having computer-executable instructions embodied thereon that, when executed, perform a method for preventing an electronic medical order for a drug dose that exceeds an upper limit, the method comprising:

receiving from a computerized individual medical data store identification of an individual and the individual's height and weight;

receiving identification of a drug to be dosed for the individual;

receiving from a computer data store a rounding rules, the target dose, and dosage algorithms for the drug, wherein the dosage algorithms include a body surface area algorithm and a weight algorithm;

receiving a selection of a dosage algorithm;

processing the dosage algorithm and the target dose with the individual's height and weight to calculate a recommended drug dosage for the individual;

processing the rounding rules to calculate the upper limit of the recommended drug dosage for the individual;

receiving an input drug dosage via an interface from a clinician of a drug dosage for the individual;

comparing the input drug dosage and the calculated recommended drug dosage to the upper limit of the recommended drug dosage to determine the input drug dosage exceeds the upper limit of the recommended drug dosage; and based on determining the input drug dosage exceeds the upper limit of the recommended drug dosage providing graphical indicia to the clinician via a graphical indicia on the interface indicating that the input drug dosage exceeds the upper limit of the recommended drug dosage.

11. The media of claim 10, further comprising:

communicating the upper limit of the recommended drug dosage for the individual to the clinician.

12. The media of claim 11, further comprising:

receiving via an interface a clinician override of the upper limit of the recommended drug dosage.

13. The media of claim 12, further comprising:

receiving via the interface text for the clinician's reason for the clinician override of the upper limit of the recommended drug.

14. The media of claim 13, further comprising:

storing in the individual's medical record the clinician override of the upper limit of the recommended drug dosage and the text for the override.

15. The media of claim 14, further comprising:

storing the clinician override to the upper limit of the recommended drug dosage in a history log for the individual for the drug.

16. The media of claim 15, further comprising placing an electronic medical order for the clinician override of the upper limit of the recommended drug dosage for the individual in an electronic medical system.

17. The media of claim 13, further comprising communicating the clinician override and the text reasoning for the clinician override to a second clinician.

* * * * *